United States Patent [19]
Hoogesteger et al.

[11] 3,983,362
[45] Sept. 28, 1976

[54] MANUAL SWITCHING MEANS FOR CONTACT LENS DISINFECTING APPARATUS

[75] Inventors: Paul A. Hoogesteger, Penfield; John Kadlecik, Macedon, both of N.Y.

[73] Assignee: Bausch & Lomb Incorporated, Rochester, N.Y.

[22] Filed: July 18, 1975

[21] Appl. No.: 597,127

[52] U.S. Cl. .................................. 219/521; 21/85; 21/93; 126/275 E; 219/451
[51] Int. Cl.² ...................... A61L 3/00; F24C 1/16
[58] Field of Search .................. 21/85, 86, 93, 105; 126/211, 217, 220, 273 R, 275 E; 219/295, 308, 337, 341, 365, 378, 439, 451, 521

[56] References Cited
UNITED STATES PATENTS

| 2,924,167 | 2/1960 | Rhodes | 219/295 X |
| 3,278,256 | 10/1966 | Skaller | 21/85 |
| 3,280,304 | 10/1966 | Shinohara et al. | 219/437 X |
| 3,413,440 | 11/1968 | Drugmand | 219/437 X |
| 3,579,262 | 5/1971 | Peeps | 21/119 X |
| 3,801,278 | 4/1974 | Wagner et al. | 21/86 |

Primary Examiner—Norman Yudkoff
Assistant Examiner—Dale Lovercheck
Attorney, Agent, or Firm—Frank C. Parker; Myron B. Kurtzman

[57] ABSTRACT

A combination comprising a push button switch or other switching means disposed in a cover of a contact lens disinfecting apparatus whereby the switching means can actuate the heating means included in the apparatus only when the cover of the apparatus is in a completely closed position.

6 Claims, 2 Drawing Figures

MANUAL SWITCHING MEANS FOR CONTACT LENS DISINFECTING APPARATUS

CROSS REFERENCES TO RELATED APPLICATIONS

An application entitled Contact Lens Asepticizing Circuit of Kurt H. Kreckel filed concurrently with this application.

Application Ser. No. 490,535, filed July 22, 1974, of John Kadlecik and John R. Williams, III entitled Contact Lens Carrying Case.

Design application Ser. No. 490,536, filed July 22, 1974, of Paul A. Hoogesteger and John Kadlecik entitled Design for a Contact Lens Storage Chamber.

Design application Ser. No. 490,537, filed July 22, 1974, of Paul A. Hoogesteger entitled Design for a Contact Lens Carrying Case.

An application entitled Apparatus & Process for Disinfection of Hydrophilic Contact Lenses of John Kadlecik and Wayne R. Manning filed concurrently with this application.

Design application filed concurrently with this application of Paul A. Hoogesteger entitled Design for Contact Lens Disinfection Apparatus.

BACKGROUND OF THE INVENTION

1. Field of the Invention

This invention relates to switching means to be employed in combination with an apparatus to be employed in the process of disinfecting hydrophilic contact lenses. More particularly, this invention relates to a switch for actuating the disinfecting process which actuation cannot occur unless the cover of the apparatus is completely closed relative to the apparatus.

2. Description of the Prior Art

Hydrophilic contact lenses being water absorbant require daily care by the patient in order to destroy pathogenic microorganisms which accumulate on and can contaminate the lenses. Daily care, i.e. disinfection, is necessary, for the microorganisms are a potential source of eye infection if they are not destroyed.

A number of methods have been suggested for disinfecting hydrophilic lenses such as, for example, boiling the lenses immersed in a saline solution for at least 10 minutes at +100°C, or chemically treating the lenses. Boiling, which requires the attention of the patient is a time consuming process and the high temperature treatment can, with the passage of time, have adverse affects upon the lens. Chemical treatment requires the utmost care since after treatment the chemicals must be properly and thoroughly flushed from the lens.

In order to destroy the pathogenic microorganisms, it is sufficient to disinfect the lens.

The physical requirements for disinfection are that the object be heated at a sufficient temperature and for a sufficient time so as to cause the destruction of pathogenic microorganisms on the lenses.

In U.S. Pat. No. 3,801,278 of Wagner et al. issued Apr. 2, 1974 an apparatus is disclosed for mass sterilization of hydrophilic lenses. The apparatus is particularly designed for the ophthalmologists and optometrists. The patent discloses and teaches that the lenses are to be sterilized. The device is not suitable for home use since it is bulky and designed around the needs of the professional who has to treat lenses in bulk. Because the lenses are sterilized the apparatus is not particularly desirable for constant use by a patient who is involved with treating only a pair of lenses. The device furthermore employs a mechanical timer for controlling its operation.

U.S. Pat. No. 3,720,402 of Cummins et al., issued May 13, 1973 describes a cleaning device for contact lenses. The device, as described, cannot effectively be employed for disinfecting since the temperature requirement for disinfecting is not obtained. The device additionally depends on a mechanical timing mechanism for its operation which, if it should not properly function, could result in the evaporation of the cleaning fluid and the concomitant adverse environment for the treated lenses.

U.S. Pat. No. 3,585,362 issued June 15, 1971 describes an apparatus which depends on the rapid conversion of a quantity of water to steam for sterilizing contact lenses. This device and others which similarly depend on the conversion of water to steam for the treatment of hydrophilic contact lenses must be carefully cared for by the patient in order to avoid the corrosion of metal parts as a result of deposits such as iron, calcium, chloride ions and the like which will form if the device is not properly cleaned after each use.

U.S. Pat. No. 3,852,032 of Urbach, issued Dec. 7, 1974, describes a method of sterilization of hydrophilic contact lenses by means of U.V. radiation. In order to avoid embrittlement and disintegration of the polymeric material constituting the contact lens, the lens material must contain ultraviolet stabilizers. The method and apparatus described is not universally applicable since few, if any, lenses comprise U.V. stabilizers.

In concurrently filed application entitled Apparatus & Process for Disinfection of Hydrophilic Contact Lenses there is described a simple device for disinfecting hydrophilic contact lenses which device is applicable for disinfecting hydrophilic lenses. The device does not depend on the production of steam for the transfer of heat from the apparatus to the lens, is easily carried about in a woman's purse or in a man's shirt pocket, and is free of mechanical timing mechanisms.

It is desirable that the apparatus include a method of activation of the disinfecting process such that said process cannot be initiated unless the apparatus is in a closed mode with relationship to its housing.

SUMMARY OF THE PRESENT INVENTION

In accordance with the present invention, there is provided a switching means to be employed in combination with a contact lens disinfecting apparatus for destroying pathogenic microorganisms that may be on and about a contact lens. Disinfection is accomplished by surrounding a contact lens carrying case containing contact lenses, typically hydrophilic contact lenses, with dry, hot air at temperatures and for at least a period of time necessary to destroy pathogenic microorganisms. The apparatus comprises a housing having a cover and a base. The cover is closable relative to the housing. The housing has an opening into which is closely fitted a heat storag-transfer block (heat member) which can be recessed so as to receive a contact lens carrying case. Upon closing the cover, an insulated compartment is formed for a contact lens carrying case. By means of a heating element enclosed in the housing the heat member is heated to a predetermined temperature. The heat absorbed by the heat member is transferred to the carrying case within the compartment at a rate so as to obtain a complete disinfecting cycle of the contact lenses within the carrying case.

In order to insure that the heating means can be actuated only when the cover is completely closed there is provided the combination of a switching means, for actuating a control means which actuates the heating means, said switching means disposed in the cover, which switching means is capable of actuating the control means only when the cover is in a completely closed position with reference to the housing.

The heat member is desirably made from a high density metal which is easily cast and coated, and has a high heat capacity as for example; zinc, brass, steel, copper, gray iron and the like. Such a material will absorb the heat and preferably provide a thermal mass in the range of 4 ounces to about 16 ounces and preferably 8 ounces. Upon obtaining the desired predetermined temperature, the selected metal will continuously release its accumulated heat at a rate and at temperatures so as to cause the interior of a contact lens carrying case to be maintained preferably within a temperature range of from +80°C to about +100°C for at least 10 minutes.

The disinfecting cycle is controlled through the selection of materials of which the heat member is constructed, the weight of the member, the predetermined temperature to which the member is heated and the insulation surrounding the material. The use of the dense metal having the proper weight will result in the metal inherently acting as the timing mechanism as well as transferring the heat from the heater to the case. If the material and its weight is such that the absorbed heat is rapidly given up, the interior of the carrying case will not be maintained at the disinfecting cycle. On the other hand, should the metal be exceedingly heavy, the disinfecting cycle will be maintained for an unnecessarily long period of time.

Upon the heat member obtaining the predetermined temperature, the heating element is deactivated by means of a selectively operable control means. Disinfection will continue since the heat member will continuously release its absorbed heat into the chamber. The device does not require a timing mechanism since the interior temperature of the carrying case and the length of time the temperature is maintained is controlled primarily by proper selection of the heat member material and the predetermined temperature.

The predetermined temperature is determined by the material of which the heat member is constructed and its size. The temperature should be selected so as to achieve the release of absorbed heat to the carrying case at a rate which will cause the disinfecting cycle to take place from about 10 to about 20 minutes and preferably from about 15 to about 20 minutes.

The weight of the heat member, in the case of it being constructed of zinc, is in the range of about 23 grams to about 248 grams. A smaller heat member will be more sensitive to ambient conditions, whereas a heavier heat member, as indicated above will maintain the disinfecting temperatures for an unnecessarily long period of time.

The predetermined temperature for a heat member constructed of zinc is about +122°C. For heat members constructed of other metals, the predetermined temperatures will be adjusted accordingly.

By employing the device in accordance with this invention, the use of steam for heat transfer is eliminated. One, furthermore, need not employ chemicals for disinfection. The device is additionally portable and safe, particularly since the heating cycle cannot occur until the cover is closed.

DESCRIPTION OF THE PREFERRED EMBODIMENTS

Figure 1:
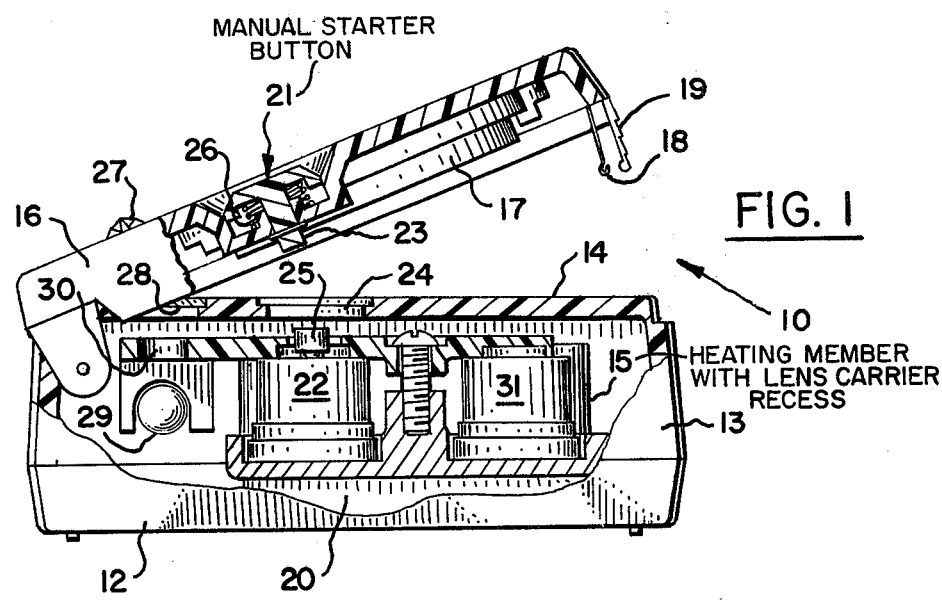
FIG. 1 is a side view of the disinfecting apparatus with its cover in an open mode.

Referring to the drawings, FIG. 1, shows the apparatus generally indicated at 10. The apparatus includes a base 12, housing 13 having an upper surface 14 into which an opening (not shown) is formed. The opening is shaped to receive a bottom portion heat member 15 having a recess or well. The heat member 15 and recess are preferably shaped in accordance with the shape of the contact lens carrying case to be received therein. The recess is preferably shallow and shaped to receive a carrying case wherein two lenses will lie substantially horizontal with respect to each other. Typically the recess will be shaped so as to receive a contact lens carrying case such as that disclosed in U.S. patent application Ser. No. 490,535 filed July 22, 1974. Should the carrying case be designed so that the lenses lie substantially vertical with respect to each other, the heat member 15 and recess would be shaped so as to form a well. The housing is provided with a suitable closure such as a hinged cover 16. However, the cover can be slidably closed or closable by other methods and means.

The cover 16 can have mounted by any suitable means a top portion heat member 17 having a recess. The top portion heat member is designed to absorb heat rapidly from the bottom heat member and transfer such heat to the carrying case and therefore is suitably constructed of a metal having a high thermal conductivity such as for example aluminum. The outer rim of the bottom heat member and the outer rim of the top heat member when the cover is in a closed configuration meet so as to form a compartment shaped to receive a contact lens carrying case.

As an alternative, heat member 15 can be constructed so as to have a flat upper surface and heat member 17 can be recessed so as to surround the top and side portions of the carrying case.

The bottom portion rim is preferably cut away in order to facilitate the placement in and removal of the carrying case with respect to the recess. A latch 18, latch cover 19 and catch (not shown) for the latch is provided so as to keep the cover or lid 16 in a secured closed position during the operation of the apparatus. Any other suitable means may be employed in order to secure the cover in a closed position during the operation of the apparatus.

Heat member 15 forming the bottom portion of the disinfecting compartment is heated by means of electrical heating element 20 which is preferably disposed on the underside of said heat member. Preferably heating element 20 is a 25 watt heater. However, higher or lower watt heat sources can be employed.

Figure 2:
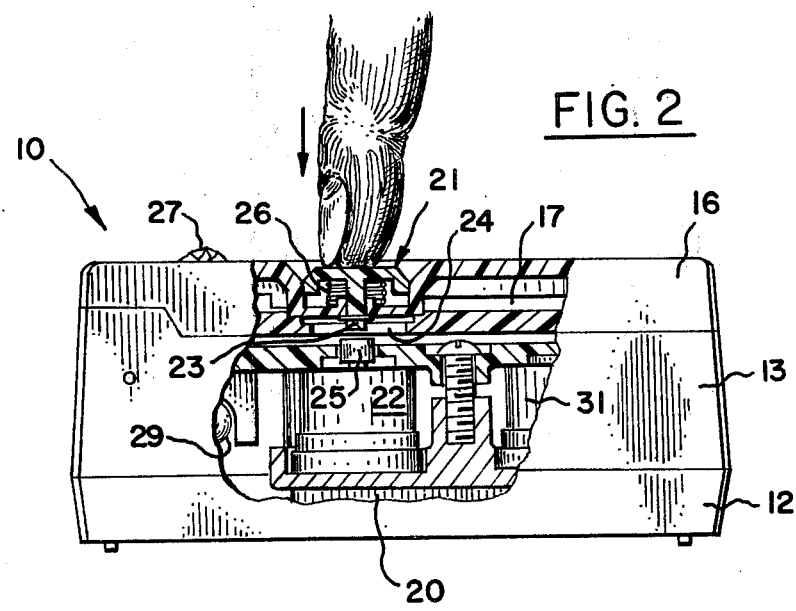
FIG. 2 is a side view of the disinfecting apparatus with its cover in a closed mode.

In accordance with this invention there is provided the combination of a switching means 21 disposed in the cover 16 for actuating a selectively operable control means such as a make or break thermostat and preferably a manual reset thermostat 22 which control means actuates the heating element 20. The switching means is disposed in a manner such that it can only cooperate with the control means 22 when the cover 16 is completely closed with reference to the housing 13. Preferably the switching means is a manually operated push button having an extension 23 projecting downwardly through the cover 16 into starter button extension apperture 24. The extension is of such length as to be just short of making contact with the actuator 25 of the control means when the cover is closed as illustrated in FIG. 2. Upon pressing the button 21, the extension cooperatively actuates the control means only when the cover is completely closed. Should the cover be even slightly ajar, the extension is of such length as to be unable to cooperate with actuator 25 thereby preventing the closing of control means switch. Preferably, the push button is spring loaded such that the button automatically springs back after release of the pressing means, i.e. the hand of the operator. In order to prevent moisture from leaking through extension apperture 24 into the electric circuitry located in the base, it is desirable to have the apperture covered by a flexible, strong sheet such as a rubber sheet. Other means such as a magnetic switch may be readily employed in place of a push button switch.

An indicator element 27 in register with a clear lens 28 and lamp 29 disposed in lamp apperture 30 beneath the lens indicates whether the apparatus is in operation. In another desirable arrangement, clear lens is removed and a lamp 36, which would extend upward through the cover, is provided thereby eliminating the need of an indicator element. Other indicator means may be suitably implied such as, for example, a temperature sensitive meter.

A thermostat 31 preferably an automatic thermostat maintains the indicator lamp 29 after the manual reset thermostat 22 deactivates the heating element 20. After the disinfecting cycle has been completed and the apparatus has cooled to a suitable temperature, thermostat 31 automatically shuts off lamp 28 thereby indicating that the disinfecting cycle is complete and the contact lens carrying case containing the lenses can be removed.

In operation, a contact lens carrying case (not shown) typically containing a pair of hydrophilic contact lenses bathed in a saline solution is placed into the bottom portion heat member 15. By means of a male plug (not shown) the apparatus is connected to a line cord (not shown) and thence to a source of electricity. The cover 16 is securely closed thereby substantially completely enclosing the carrying case in a substantially heat tight compartment. The operator presses the starter button 21 which extends through the actuator apperture 24 thereby engaging the actuator 25 of the manual reset thermostat 25. The manual reset thermostat 22 actuates the heating element 20. The heating element 20 heats the heat member 15 until the heat member, which is preferably constructed of zinc, reaches a temperature of about +122°C. The manual reset thermostat 22 thereupon deactivates the heating element 20. The interior of the carrying case is closely surrounded by the heating member and preferably the bottom and side walls of the carrying case are surrounded by the bottom portion heating member. The heat members transfer their absorbed heat to the carrying case thereby causing the temperature interior the carrying case to rise. The rate of heat transfer which, as explained hereinbefore, is such that the interior of the carrying case is maintained at sufficient time and temperature so as to obtain a disinfecting cycle.

In order to indicate that apparatus 10 is in operation, the indicator lamp 29 is automatically turned on upon activation of the heater element 20. When heat member 15 initially reaches a temperature of about +90°C, automatic thermostat 31 closes a switch so as to control the indicator lamp after the manual reset thermostat 22 opens. When the heating member 15 falls to a temperature of about +52°C, the indicator lamp 29 is automatically switched off by the thermostat 31 which opens thereby signaling that the lenses have been through a complete disinfecting cycle.

Disinfecting cycle is understood to mean that period of time at the necessary temperatures required to destroy the pathogenic microorganisms on and about the contact lens.

We claim:

1. A contact lens disinfecting apparatus comprising a housing having a base and a movable cover, the base portion including a heat storage-transfer means and heating means, the housing when the cover is in closed position forming a chamber for a contact lens carrying case, the apparatus further including the combination of a switching means and selectively operable control means for activating the heating means, the switching means disposed in the cover and extending upwardly and downwardly through the cover, the downward end of the switching means being minutely spaced apart from the control means when the cover is in closed position but substantially spaced apart from the control means when the cover is not closed, said switching means being capable of actuating the control means when the cover is in closed position but unable to actuate the control means when the cover is not completely closed.

2. The disinfecting apparatus of claim 1 wherein the selectively operable control means is a manual reset thermostat.

3. The disinfecting apparatus of claim 2 wherein the switching means is manually operated.

4. The disinfecting apparatus of claim 3 wherein the switching means is disposed so as to be manually operatable at the upward end of said means.

5. The disinfecting apparatus of claim 4 wherein the switching means is a push button.

6. The disinfecting apparatus of claim 5 wherein the push button switch is spring loaded.

* * * * *